United States Patent [19]

Hellstrom et al.

[11] Patent Number: 5,233,195
[45] Date of Patent: Aug. 3, 1993

[54] METHODS AND APPARATUS FOR MEASURING CHARACTERISTICS OF MOVING WEBS

[75] Inventors: Ake A. Hellstrom, Columbus, Ohio; Wim Muller, Westendorp, Netherlands; Steven P. Sturm; Alan M. Reid, both of Columbus, Ohio

[73] Assignee: ABB Process Automation, Inc., Columbus, Ohio

[21] Appl. No.: 841,366

[22] Filed: Feb. 25, 1992

[51] Int. Cl.$^5$ .................. G01N 23/16; G21F 5/015
[52] U.S. Cl. .................. 250/360.1; 250/308; 250/358.1; 250/359.1; 250/496.1; 250/497.1; 250/498.1
[58] Field of Search ............ 250/360.1, 359.1, 358.1, 250/498.1, 497.1, 496.1, 308

[56] References Cited

U.S. PATENT DOCUMENTS

| | | | |
|---|---|---|---|
| 3,087,061 | 4/1963 | Dukes et al. | 250/308 |
| 3,240,940 | 3/1966 | Dukes et al. | 250/359.1 |
| 3,560,748 | 4/1967 | Hatten | 250/496.1 |
| 3,662,174 | 5/1972 | McMullen et al. | 250/358.1 |
| 3,742,216 | 6/1973 | Hahn | 250/308 |
| 3,742,218 | 6/1973 | Fleming, Jr. | 250/381 |
| 3,757,122 | 9/1973 | Bossen et al. | 250/358.1 |
| 3,795,804 | 3/1974 | Scheininger et al. | 250/498.1 |
| 3,828,190 | 8/1974 | Dahlin et al. | 250/308 |
| 4,160,204 | 7/1979 | Holmgren et al. | 324/207.16 |
| 4,542,297 | 9/1985 | Hold | 250/360.1 |
| 4,678,915 | 7/1987 | Dahlquist et al. | 250/358.1 |
| 4,692,616 | 9/1987 | Hegland et al. | 250/252.1 |
| 5,010,766 | 4/1991 | Typpo | 73/159 |
| 5,077,478 | 12/1991 | Walford | 250/359.1 |

FOREIGN PATENT DOCUMENTS

| | | | |
|---|---|---|---|
| 710339 | 9/1981 | U.S.S.R. | 250/358.1 |

OTHER PUBLICATIONS

Japanese Regulatory Drawing dated Jun. 1, 1989.
AccuRay 1190, Basis Weight Sensors, ABB Process Automation Brochure, [©1991].
Uptime, Basis Weight Sensors, Robin Process Management Systems Brochure, [undated].
Ohmart Advertisement, [undated].
Model 4403, Basis Weight Sensor, Impact Systems, Inc. Brochure, [©1989].
Iso Therm Scanner Model 2100, Measurex Advertisement, [undated].
Betameter, Valment Automation Brochure, [undated].
Iso Therm Scanner Designed for Hot Environment, *PIMA* Magazine, Feb. 1991.
Digitector 111, Basis Weight Sensor 2201, Measurex Brochure, [undated].
Digitector Basis Weight Sensor 2262, Measurex Brochure, [undated].
"Advances in Gaging Precision Give Lift to Specialty Performance Films", *Modern Plastics*, Feb. 1989.
Commercially available Web Measurement System, see description of system on p. 2 of Information Disclosure Statement.

*Primary Examiner*—Constantine Hannaher
*Attorney, Agent, or Firm*—Killworth, Gottman, Hagan & Schaeff

[57] ABSTRACT

Characteristics of moving webs are measured using a radiation source shutter which is rotatably movable between an opened-shutter position and a closed-shutter position and structured to permit access to the radiation source in the closed-shutter position. The source is configured to produce a fan-shaped radiation beam which passes through the web to a detector. The sizing of the fan-shaped beam and the detector together with the spacing the source and the detector are such that the beam width is substantially less than the detector while its length is greater than the detector. This novel beam shaping, detector arrangement provides composition insensitivity, increases solid beam angle and superior streak detection by aligning the beam length dimension with the direction of web movement. Alignment insensitivity is obtained by tuning the radiation beam using concentric rings or crossed strips of material which is semi-transparent to the radiation to compensate for geometric characteristics of the radiation source/beam and the detector. Air within an open portion of a measuring column extending between the radiation source and detector is conditioned and also used to condition electronics associated with the detector. The gap between the radiation source and the detector is monitored and used to compensate for variations in the measuring column air mass due to gap variations.

33 Claims, 8 Drawing Sheets

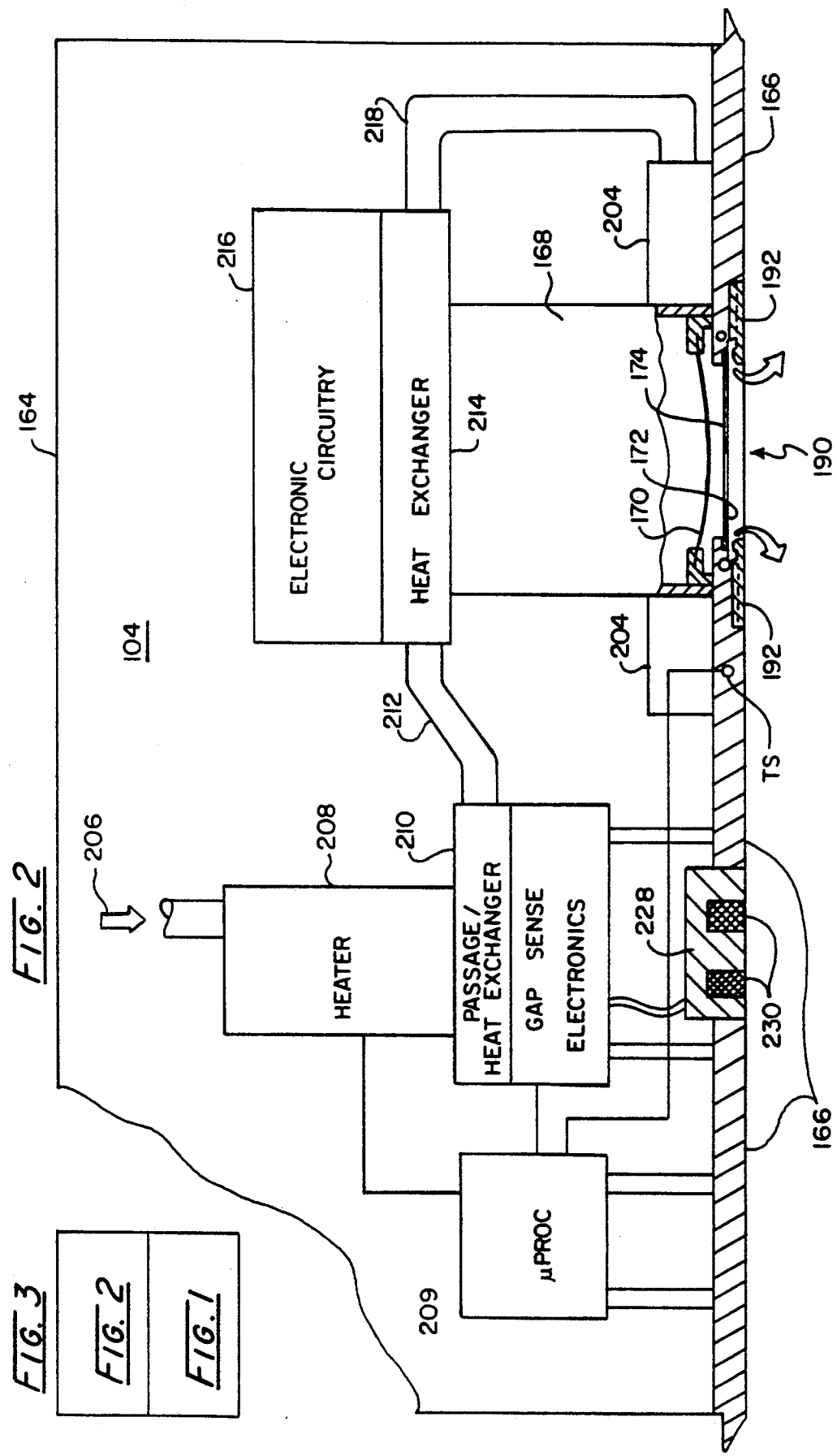

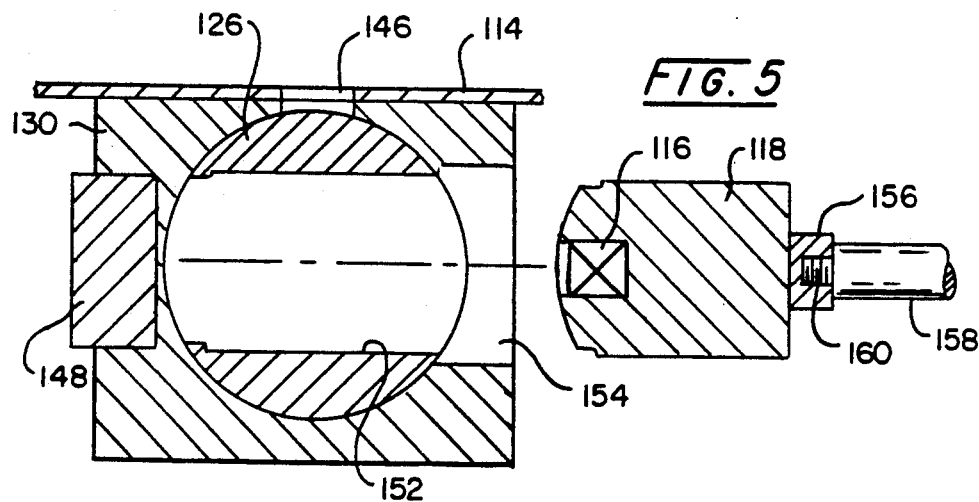
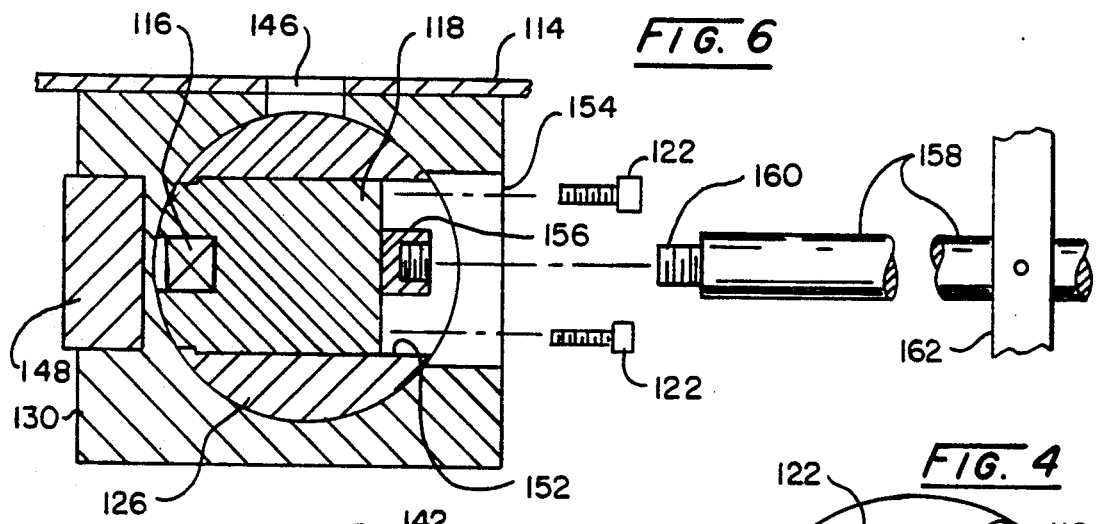
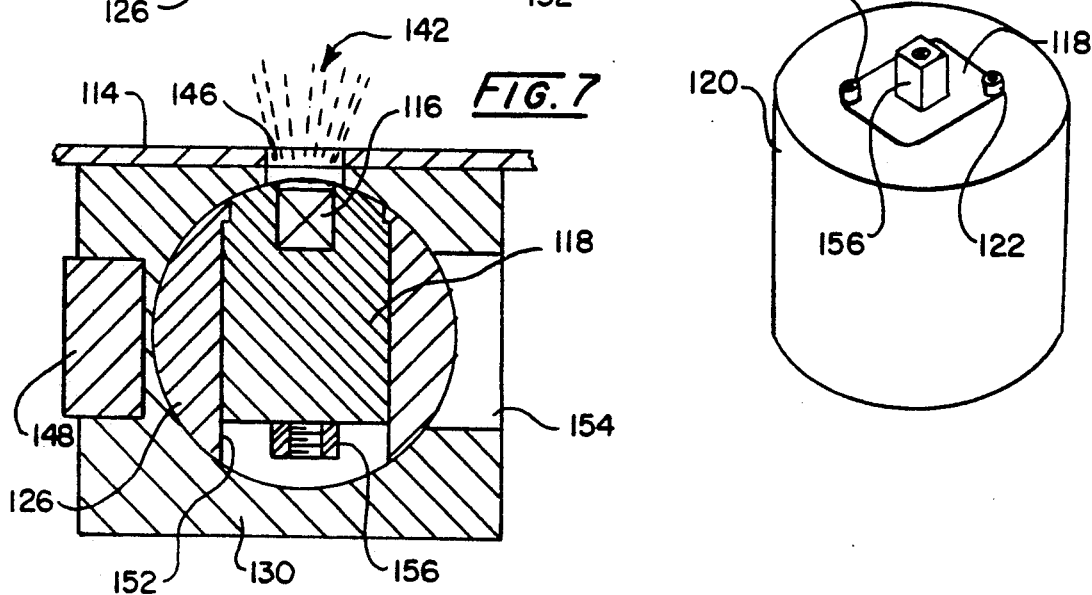
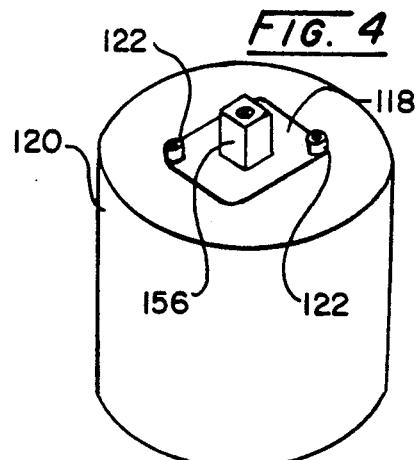

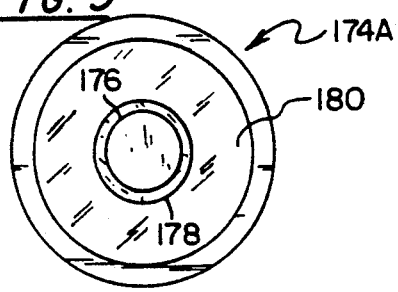
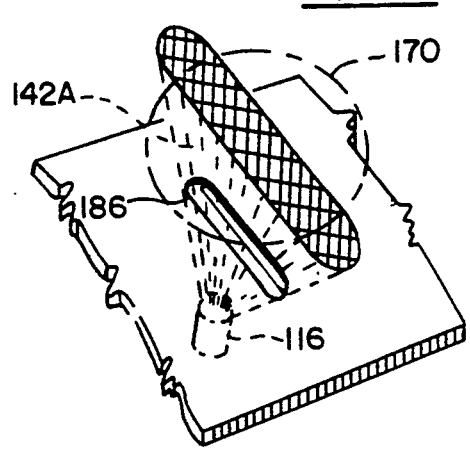
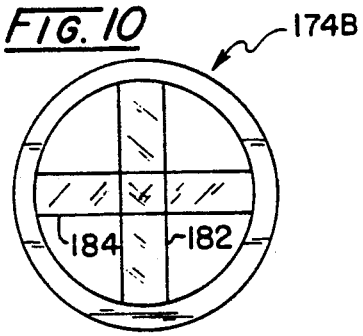
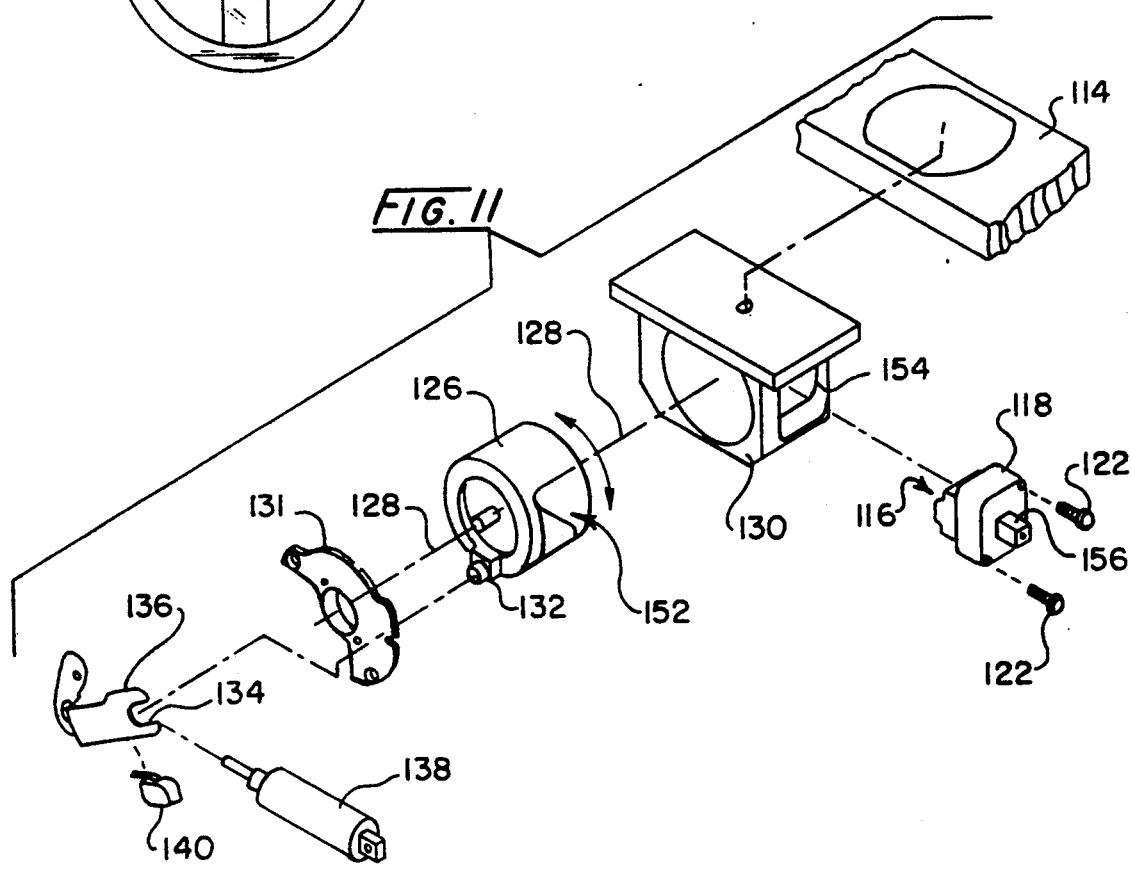

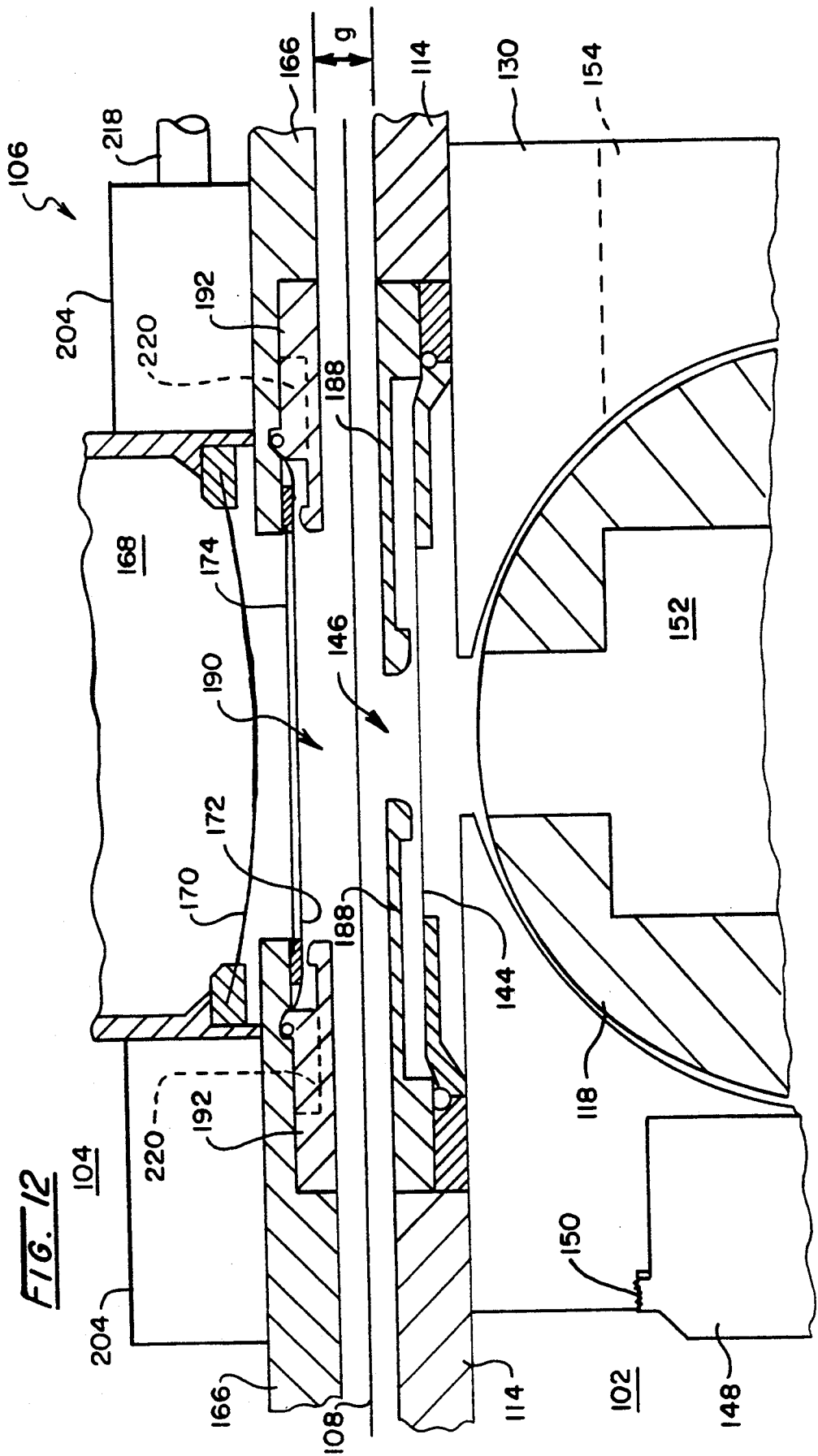

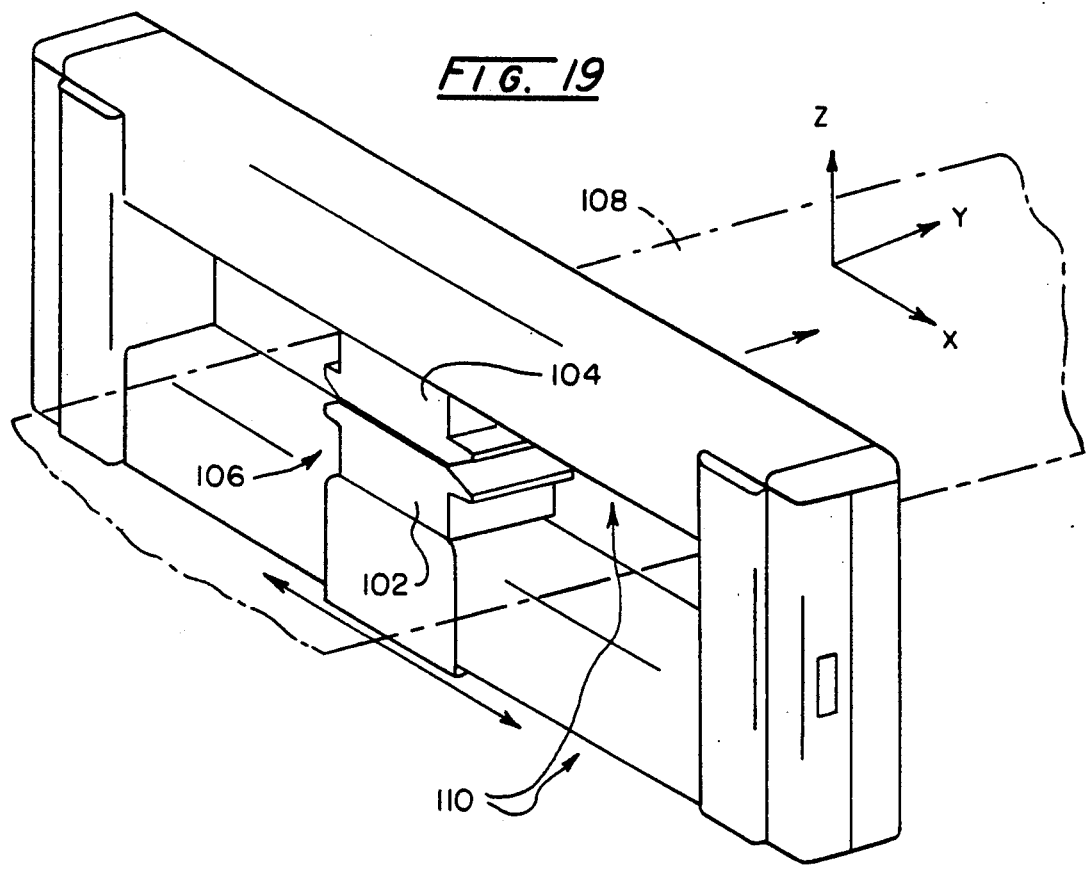
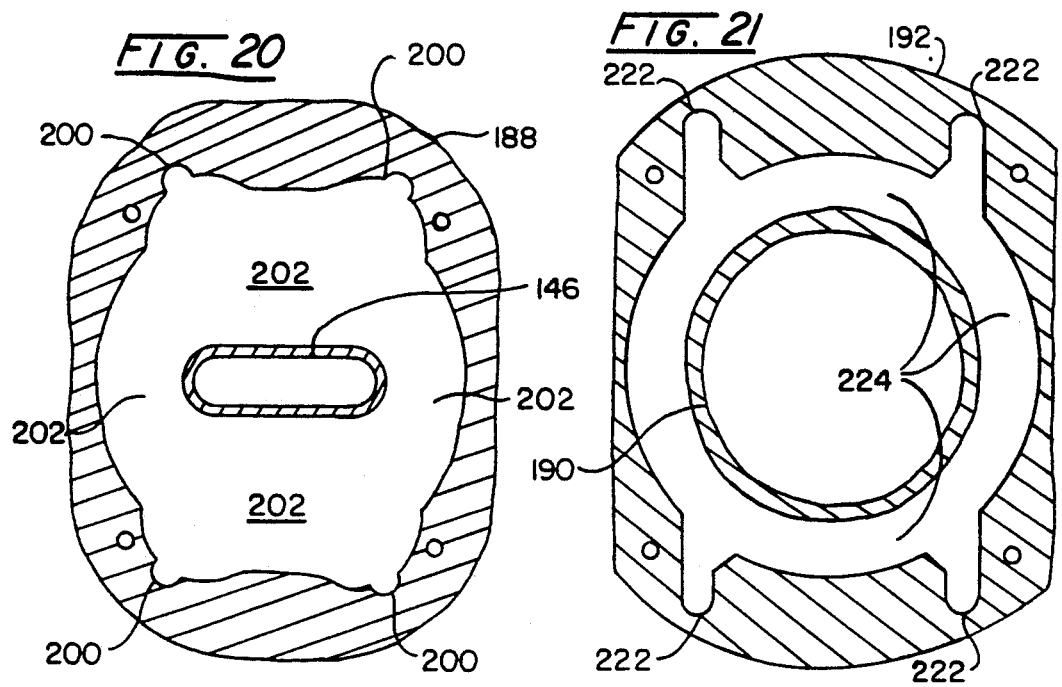

METHODS AND APPARATUS FOR MEASURING CHARACTERISTICS OF MOVING WEBS

BACKGROUND OF THE INVENTION

The present invention relates generally to measuring characteristics of a web of moving sheet material and, more particularly, to a number of improved methods and apparatus which individually and cooperatively enhance performance of such measurements. For example, an easily accessible radiation source may be mounted in a rotary shutter for generating a measuring radiation beam and providing a short air gap to an associated radiation detector. The radiation beam may be tuned for improved measuring performance and may be fan-shaped and sized relative to the radiation detector such that the ends of the beam overlap the detector with the system being tuned for improved performance. The improvements of the present invention provide superior streak detection, composition and alignment insensitivity, reliability, accuracy and stability.

Systems for measuring characteristics of moving webs of a wide variety of sheet materials are well known in the art. For example, characteristics are commonly measured by scanning a measurement head transversely back and forth across a moving web. The measurement head includes a source of radiation which is supported on one side of the web of material, and a detector for sensing the radiation supported directly opposite to the source. The radiation is attenuated by the web of sheet material such that the amount of radiation received by the detector is representative of a characteristic which is to be measured. The type of radiation may be selected dependent upon the material making up the web and the characteristic or characteristics to be measured.

While prior art systems have been effectively used for a substantial period of time, the requirements for the performance of these systems has been constantly increasing. As an example, in the paper making industry, the specifications for paper making process variability have been tightened by at least an order of magnitude over the last twenty years. The increasing performance standards require improved sensors, systems employing the sensors and automatic control techniques which remove a substantial portion of error inherent in subjective human control.

The task of meeting the constantly advancing requirements has been exacerbated by a corresponding trend towards operating web making processes at higher temperatures, higher speeds and often with more recycled and dusty materials. All of these operating trends contribute to make an already hostile environment for web measurement systems even more hostile.

Improving the various aspects of web measurement systems has been difficult. For example, if a basis weight sensor is designed for improved performance in one area, such as composition insensitivity, the design "improvement" may cause the system to be more noise or alignment sensitive. These design problems are due to the physics of radiation interaction with the materials making up the webs which are to be measured.

It is thus apparent that there is an ongoing need for improved systems for measuring web characteristics. Preferably, improvements to web measuring systems could be combined to provide overall improved measurement and also be individually applicable for overcoming specific measurement problems.

SUMMARY OF THE INVENTION

This need is met by the methods and apparatus of the present invention wherein characteristics of a moving web of material are measured using a number of improvements in the measuring art. For example, a fan-shaped beam of radiation may be directed through the web of material to impinge upon a detector with ends of the beam extending beyond the detector. The sizing of the fan-shaped beam and the detector together with the spacing between a radiation source creating the beam and the detector are such that the width of the beam is substantially less than the radiation receiving portion of the detector and the length of the beam is greater than the radiation receiving portion of the detector. Thus, the relative sizing of the beam to the radiation receiving portion of the detector is such that the width of the beam is well within the radiation detection portion of the detector while both ends of the beam extend beyond the radiation receiving portion of the detector for all measurement conditions.

This novel beam shaping and detection arrangement provides composition insensitivity and also superior streak detection by aligning the length dimension of beam with the direction of movement or machine direction of the web. Composition insensitivity can be peaked or optimized by varying the length dimension of the beam. With this beam/detector arrangement, the beam is narrow in the cross direction, which is essential for reliable streak detection, and also a large solid beam angle is provided to maintain an acceptable signal-to-noise (S/N) ratio.

Additional improvement in alignment insensitivity is obtained by tuning the radiation beam to compensate for geometric characteristics of the radiation source/beam and the detector. Beam tuning is performed by provided radiation attenuating material generally centered on the radiation detector between the radiation source and the detector. In one embodiment of such tuning means, at least two concentric disks formed from one or more materials which are semi-transparent to the radiation being used are positioned over the center of the radiation detector between the radiation source and the radiation detector. In another embodiment of the tuning means, two crossed strips formed from one or more materials which are semi-transparent to the radiation being used are positioned over the center of the radiation detector between the radiation source and the radiation detector. The crossed strips are oriented at substantially 90° relative to one another and each strip preferably extends substantially entirely across the radiation receiving portion of the detector.

Reliability and consistency are ensured by conditioning the open portion of the column extending between the radiation source and the radiation detector through which the web of material to be measured passes. A radiation source window and a detector window are provided and recessed into a radiation source sensor plate and a detector sensor plate, respectively. The radiation source sensor plate defines a beam source aperture beyond the radiation source window; and, the detector sensor plate defines a beam receiving aperture beyond the detector window. A first air manifold is formed to pass conditioned air over the radiation source window and out the beam source aperture; and, a second air manifold is formed to pass conditioned air over the detector window and out the beam receiving aperture.

This arrangement provides a number of operating improvements. Initially, the air column is maintained at a substantially controlled temperature to help achieve accurate measurements of the web. In addition, the air serves to wipe the windows and reduce the entrance and build-up of dirt on the recessed windows by providing a positive outflow of air in the direction of the web. The air further operates as an air bearing to float the web between the two plates as the windows are maintained clean by the air flow. This air bearing helps to maintain the web centered between the plates, reduces web flutter, substantially eliminates web contact with the plates and permits a shorter gap to be maintained between the beam source and the detector which enhances measurement operations. To further stabilize the present invention, the conditioned air is first passed over electronic circuitry associated with the detector before being passed to the second air manifold.

The gap between the radiation source and the radiation detector is also measured such that gap variations can be compensated. Gap measurement uses a temperature stable ferrite cup/winding combination which is positioned across the web from a ferrite sheet. The spacing between the cup/winding combination and the ferrite sheet vary the inductance presented by the winding which is used to control an LC oscillator the oscillating frequency of which is used to determine the gap.

In the preferred form of the invention, the radiation source is rotatably movable between an exposed, web monitoring or opened-shutter position and an enclosed or closed-shutter position. This rotary shutter arrangement further reduces the spacing between the beam source and the detector and permits reduced sizing of the system components. In addition, the preferred arrangement of the rotary shutter is structured to facilitate insertion and removal of the radiation source by permitting these operations while the shutter is in its closed position.

In accordance with one aspect of the present invention, a method of measuring characteristics of a web of sheet material moving in a first direction and having first and second sides comprise the steps of: positioning a radiation source on the first side of the web of sheet material; positioning a detector of the radiation on the second side of the web of sheet material substantially directly opposite to the radiation source; shaping radiation emitted from the radiation source to form a beam defining a narrow band of radiation having an expanding length and width as the beam travels from the radiation source; spacing the detector from the radiation source such that the width of the band is substantially less than a radiation receiving portion of the detector and the length of the band is greater than the radiation receiving portion of the detector with the result that ends of the band extend beyond opposite sides of the radiation receiving portion of the detector; reciprocally scanning the radiation source and the detector in a second direction substantially perpendicular to the first direction; detecting radiation received by the detector; and, determining characteristics of the web of sheet material to be measured from radiation detected by the detector.

To provide superior streak detection, the method further comprises the step of orienting the beam such that the length of the narrow band defined by the beam is substantially aligned with the first direction and the width of the narrow band is substantially aligned with the second direction. Composition insensitivity is improved for the method by including the step of tuning the radiation beam to compensate for geometric characteristics of the radiation source and the detector.

To more closely associate the radiation source and the detector of the invention, the method may further comprise the step of supporting the radiation source in a rotating shutter. Preferably, the method further comprises the step of forming the rotating shutter to permit access to the radiation source when the shutter is rotated to a closed position to thereby facilitate placement of the radiation source into the rotating shutter and removal of the radiation source from the rotating shutter.

The method may further comprise the steps of: providing a radiation source sensor plate for performing the step of positioning the radiation source, the radiation source sensor plate defining a beam source aperture through which the beam is emitted; providing a recessed radiation source window within the radiation source sensor plate; and, defining an air manifold associated with the radiation source sensor plate for routing conditioned air over the recessed radiation source window and outwardly through the beam source aperture. In addition, the method may further comprise the steps of: providing a detector sensor plate for performing the step of positioning the detector, the detector sensor plate defining a beam receiving aperture through which the beam is received; providing a recessed detector window within the detector sensor plate; and, defining an air manifold associated with the detector sensor plate for routing conditioned air over the recessed detector window and outwardly through the beam receiving aperture.

To further enhance the stability and reliability of the invention, the method may further comprise the steps of: providing electronic circuit means associated with the detector for processing signals representative of radiation detected by the detector to determine characteristics of the web; routing conditioned air to the electronic circuit means to regulate the temperature of the electronic circuit means and thereby stabilize web characteristic measurements; and, routing the conditioned air to the air manifold from the electronic circuit means.

In accordance with another aspect of the present invention, a method of measuring characteristics of a web of sheet material moving in a first direction and having first and second sides comprises the steps of: supporting a rotating shutter on said first side of said web of sheet material, said shutter being rotatably movable between an opened measuring position wherein a radiation source receiving cavity is directed toward said web of sheet material and a closed position wherein said radiation source receiving cavity is directed toward a radiation shield; supporting a detector of said radiation on said second side of said web of sheet material substantially directly opposite to said shutter; rotating said shutter to said closed position; inserting a radiation source into said radiation source receiving cavity in said rotating shutter; rotating said shutter to said opened position; reciprocally scanning said rotating shutter and said detector in a second direction substantially perpendicular to said first direction; detecting radiation received by said detector from said radiation source; and, determining characteristics of said web of sheet material to be measured from radiation detected by said detector.

In accordance with yet another aspect of the present invention, a method of measuring characteristics of a web of sheet material moving in a first direction and having first and second sides comprises the steps of: positioning a radiation source on said first side of said web of sheet material; positioning a detector of said radiation on said second side of said web of sheet material substantially directly opposite to said radiation source; tuning a radiation beam emitted by said radiation source to compensate for geometric characteristics of said radiation source and said detector; reciprocally scanning said radiation source and said detector in a second direction substantially perpendicular to said first direction; detecting radiation received by said detector; and, determining characteristics of said web of sheet material to be measured from radiation detected by said detector.

The step of tuning in the foregoing methods may comprise the steps of: positioning a first disk of material which is semi-transparent to the radiation at a substantially central point of receipt of the beam by the detector; and, positioning a second disk of material which is semi-transparent to the radiation at a substantially central point of receipt of the beam by the detector, the second disk being larger than the first disk and positioned concentric with the first disk. Alternately, the step of tuning may comprise the steps of: positioning a first strip of material which is semi-transparent to the radiation in substantial alignment with the length of the narrow band defined by the beam, the first strip being substantially centered upon and extending along at least a substantial portion of the length of the narrow band; and, positioning a second strip of material which is semi-transparent to the radiation substantially perpendicular to the first strip in substantial alignment with the center of the narrow band defined by the beam, the second strip extending along at least a substantial portion of the width of the narrow band.

In accordance with still another aspect of the present invention, a system for measuring characteristics of a web of sheet material moving in a first direction and having first and second sides comprises radiation source means positioned on the first side of the web of sheet material for emitting a beam of radiation. Detector means for detecting the radiation, the detector means are positioned on the second side of the web of sheet material substantially directly opposite to the radiation source means. Aperture means are associated with the radiation source means for shaping the beam of radiation to form a beam defining a narrow band of radiation having an expanding length and width as the beam travels from the radiation source means. The radiation source means, the detector means and the aperture means are sized and spaced relative to one another such that the width of the narrow band of radiation is substantially less than the detector means and the length of the narrow band of radiation is greater than the detector means with ends of the narrow band of radiation extending beyond opposite sides of the detector means. Scanner means provide for reciprocally scanning the radiation source means and the detector means across the web of material in a second direction substantially perpendicular to the first direction.

To provide superior streak detection, the aperture means is aligned to emit the beam such that the length of the beam is substantially aligned with the first direction. The system further comprises tuner means for tuning the beam of radiation to compensate for geometric characteristics of the radiation source means and the detector means to enhance composition insensitivity.

In one embodiment, the tuner means comprises a tuning component supported between the radiation source means and the detector means. The tuning component comprises a first disk of material which is semi-transparent to the radiation and supported at a substantially central point of receipt of the beam by the detector means, and a second disk of material which is semi-transparent to the radiation and supported at a substantially central point of receipt of the beam by the detector means, the second disk being larger than the first disk and positioned concentric with the first disk.

In another embodiment, the tuning means comprises a tuning component supported between the radiation source means and the detector means. The tuning component comprises a first strip of material which is semi-transparent to the radiation and supported in substantial alignment with the length of the narrow band defined by the beam, the first strip being substantially centered upon and extending along at least a substantial portion of the length of the narrow band, and a second strip of material which is semi-transparent to the radiation and supported substantially perpendicular to the first strip in substantial alignment with the center of the narrow band defined by the beam, the second strip extending along at least a substantial portion of the width of the narrow band.

To more closely associate the radiation source and the detector of the invention, the system may further comprise rotating shutter means for supporting the radiation source means. Preferably, the rotating shutter means comprises a cylindrical member mounted for rotation about a central axis. The cylindrical member is rotatable about its central axis between a shutter opened position and a shutter closed position and includes a radiation source means receiving cavity extending through the cylindrical member. The radiation source receiving cavity is accessible when the cylindrical member is rotated to the shutter closed position for insertion and removal of the radiation source means while the shutter is in its closed position.

The system may further comprise a radiation source sensor plate associated with the radiation source means. The radiation source sensor plate supports the aperture means which defines a beam source aperture through which the beam is emitted. A radiation source window is recessed within the radiation source sensor plate adjacent to the beam source aperture. First air manifold means is defined by the aperture means and the radiation source sensor plate to route conditioned air over the recessed radiation source window and outwardly through the beam source aperture. In addition, the system may further comprise a detector sensor plate associated with the detector means. The detector sensor plate supports aperture means for defining a beam receiving aperture through which the beam is received. A detector window is recessed within the detector sensor plate. Second air manifold means is associated with the detector sensor plate and the second air manifold means and the detector sensor plate cooperatively route conditioned air over the recessed detector window and outwardly through the beam receiving aperture.

The system may further comprise electronic circuit means associated with the detector means for processing signals representative of radiation detected by the detector means to determine characteristics of the web. To further enhance the stability and reliability of the invention, conduit means for routing conditioned air initially to the electronic circuit means to regulate the temperature of the electronic circuit means and thereby stabilize web characteristic measurements performed by the system and then to the second air manifold means are provided. Preferably, the conduit means includes heat exchanger means associated with the electronic circuit means for regulating the temperature of the electronic circuit means with no direct contact between the conditioned air and the electronic circuit means.

In accordance with another aspect of the invention, a system for measuring characteristics of a web of sheet material moving in a first direction and having first and second sides comprises radiation source means for emitting a beam of radiation. Rotating shutter means provide for supporting the radiation source means on the first side of the web of sheet material for emitting the beam of radiation through the web, the rotating shutter means comprising a housing member mounted for rotation about an axis, the housing member being rotatable about the axis between a shutter opened position and a shutter closed position and including a radiation source means receiving cavity extending through the housing member which cavity is accessible for insertion and removal of the radiation source means when the housing member is rotated to the shutter closed position. Detector means are positioned on the second side of the web of sheet material substantially directly opposite to the radiation source means for detecting the radiation when the rotating shutter means is in the opened position. Scanner means reciprocally scan the rotating shutter means and the detector means across the web of material in a second direction substantially perpendicular to the first direction.

In accordance with yet another aspect of the invention, a system for measuring characteristics of a web of sheet material moving in a first direction and having first and second sides comprises radiation source means positioned on the first side of the web of sheet material for emitting a beam of radiation. Detector means are positioned on the second side of the web substantially opposite the radiation source for detecting the beam of radiation. Tuner means are provided for tuning the beam of radiation to compensate for geometric characteristics of the radiation source means and the detector means. Scanner means reciprocally scan the radiation source means and the detector means across the web of material in a second direction substantially perpendicular to the first direction.

In accordance with yet still another aspect of the present invention, a system for measuring characteristics of a web of sheet material moving in a first direction and having opposite sides comprises radiation source means positioned on one side of the web of sheet material for emitting a beam of radiation and detector means for detecting the radiation, the detector means being positioned on a side opposite to the one side of the web of sheet material substantially directly opposite to the radiation source means and spaced therefrom by a gap. Gap sensing means are provided for measuring the gap between the radiation source and detector means to compensate for variations in the gap or air column extending between the radiation source means and the detector means. The gap sensing means comprises a ferrite cup positioned on one side the web of sheet material having a winding positioned therein. A ferrite plate is positioned opposite to the ferrite cup, and the ferrite plate is circular and larger in diameter than the ferrite cup. An LC oscillator circuit is connected to the winding for generating a signal having a frequency representative of the gap between the source means and the detector means. Frequency to voltage converter means connected to the LC oscillator circuit generate a voltage representative of the gap. Scanner means provide for reciprocally scanning the radiation source means and the detector means across the web of material in a second direction substantially perpendicular to the first direction. Preferably, the ferrite cup and the ferrite plate are constructed from temperature stable ferrite material having very high permeability.

It is thus an object of the present invention to provide improved methods and apparatus for measuring characteristics of webs of material; to provide improved methods and apparatus for measuring characteristics of webs of material wherein a fan-shaped radiation beam is aligned with the direction of movement of a web and is sized in coordination with a radiation detector to be narrower than the detector and longer than the detector for improved composition insensitivity; to provide improved methods and apparatus for measuring characteristics of webs of material wherein system radiation beam tuning is performed by at least two concentric circles or crossed strips of one or more materials which are semitransparent to radiation from the radiation source with the circles or crossed strips being centered upon a central point of radiation receipt of the detector; and, to provide improved methods and apparatus for measuring characteristics of webs of material wherein a radiation source is mounted in a rotary shutter for removal and insertion while the rotary shutter is in a closed position.

Other objects and advantages of the invention will be apparent from the following description, the accompanying drawings and the appended claims.

BRIEF DESCRIPTION OF THE DRAWINGS

FIG. 2 is a partially sectioned side view of a detector head including various aspects of the present invention;

FIG. 3 illustrates the orientation of FIGS. 1 and 2 to form a web measurement system operable in accordance with the present invention;

FIG. 4 is a perspective view of a radiation source holder inserted into a health shield;

FIGS. 5-7 schematically illustrate insertion/removal of a source and source holder into a rotary shutter and operation of the shutter between closed and opened positions;

FIG. 8 is a perspective view illustrating generation and detection of a fan-shaped beam in accordance with the present invention;

FIGS. 9-10 show two embodiments of tuner means in accordance with the present invention for tuning a beam or radiation generated by a radiation source;

FIG. 11 is an exploded perspective view illustrating a rotary shutter and radiation source/source holder for use in the present invention;

FIG. 12 is a partially sectioned side view on an expanded scale of the interrelation between the source head of FIG. 1 and the detector head of FIG. 2 with a web of material passing therebetween;

FIG. 19 is a perspective view of a measuring system scanning frame or platform for use in the present invention;

FIGS. 20 and 21 are partially sectioned views of a radiation source aperture plate and a detector aperture plate showing conditioned air entry and exit areas for the source aperture and detector aperture, respectively;

DETAILED DESCRIPTION OF THE INVENTION

Figure 1:
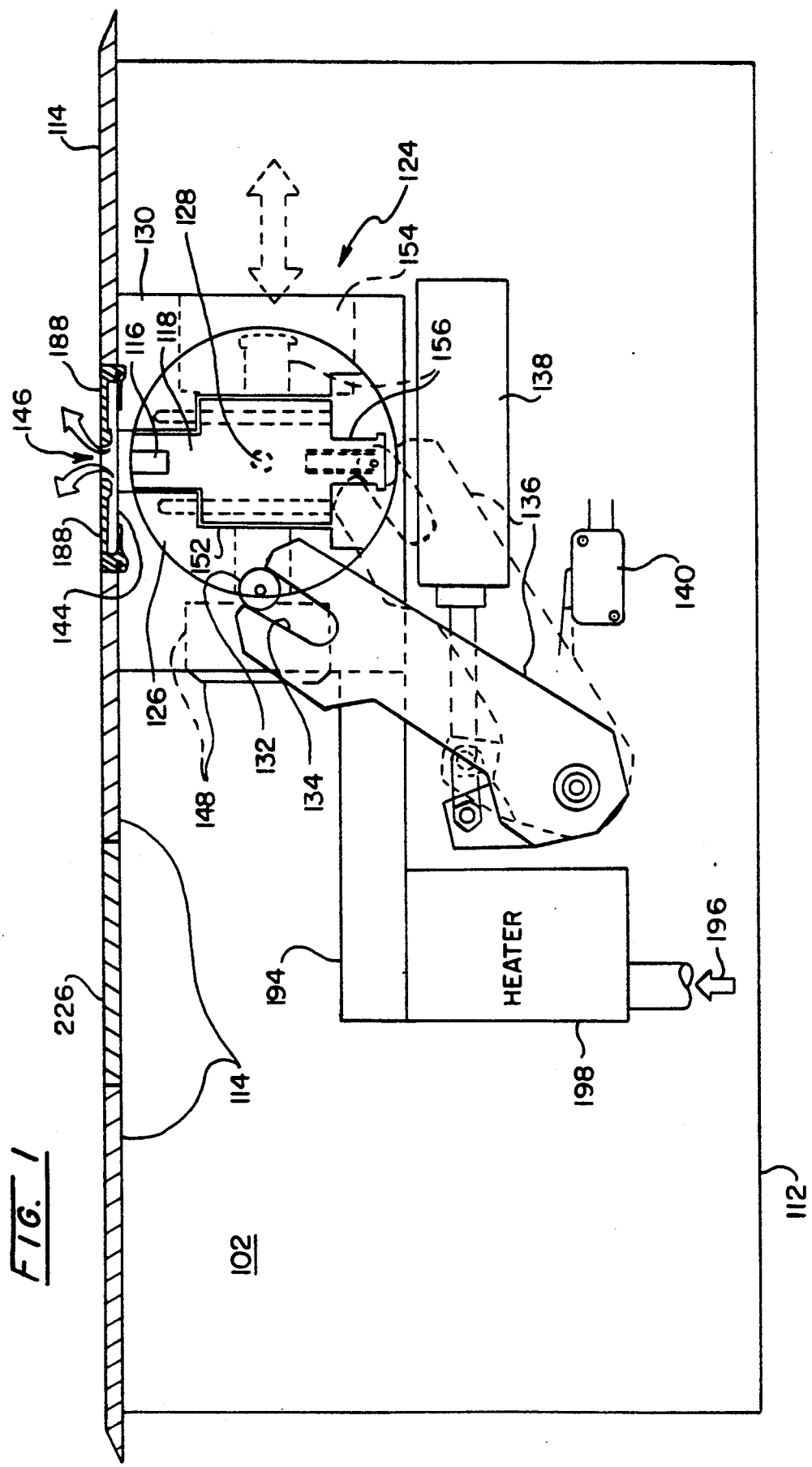
FIG. 1 is a partially sectioned side view of a source head including various aspects of the present invention.

FIGS. 1 and 2 illustrate a source head 102 and a detector head 104, respectively, operable in accordance with the present invention. The source head 102 is typically mounted below the detector head 104 as illustrated by FIGS. 3 and 19 to form a web measuring system 106 for measuring various characteristics of a web 108 of material as it is being manufactured. As shown in FIG. 19, the source head 102 and detector head 104 are positioned on opposite sides of the web 108 in fixed vertical relationship to one another and moved or scanned transversely across the web 108 by a stable foundation or platform 110 in a conventional manner.

The source head 102 of FIG. 1 comprises a housing 112 which has an upper surface defined by a radiation source sensor plate 114. Radiation source means comprises a source 116 of radiation which, for example, can be a beta emitting radioisotope such as Sr-90, Kr-85 or Pm-147, a source of x-rays, or other source appropriate for a given measurement application. The source 116 is supported in a source holder 118 shown in FIGS. 1 and 4–7. The source 116 and source holder 118 are retained within a health shield 120 which provides radiation shielding in all directions for safe storage or handling when not installed in the source head 102. The source holder 118 is securely retained within the health shield 120 by bolts 122 which are also used to secure the source holder 118 into the source head 102.

The source 116 and source holder 118 are mounted into rotating shutter means 124 which comprises a cylindrical member or rotary shutter 126 which is mounted for rotation about a central axis 128 in a rotary shutter housing 130 via a bearing support plate 131, see FIGS. 1 and 11. The rotary shutter 126 includes a rotation control pin 132 which is engaged within a channel 134 of a rotation control lever 136. The lever 136 forms part of a rotation control linkage which is coupled to a hydraulic control cylinder 138 or other appropriate source of motive force. The control cylinder 138 is extended to move the rotary shutter 126 to a closed position shown by the partial dotted line drawing of FIG. 1 and by FIGS. 5, 6 and 11. The cylinder 138 is withdrawn to move the rotary shutter 126 to an opened position for web measurement operations shown by the solid line drawing of FIG. 1 and by FIGS. 7 and 12. An electrical switch 140 is engaged by the rotation control lever 136 to positively signal movement of the rotary shutter 126 to its closed position.

When the rotary shutter 126 is in its opened position, the radiation source 116 is able to emit a beam of radiation 142 through a recessed radiation source window 144 and aperture means which defines a beam source aperture 146. When the rotary shutter 126 is in its closed position, the radiation source 116 is substantially sealed within the rotary shutter housing 130 and is substantially centered upon and directed toward a generally cylindrical radiation shield block 148. The shield block 148 is removably secured within the rotary shutter housing 130 for example by screw threads 150, see FIG. 12, such that it can be removed and replaced to correspond to and properly shield whatever type of radiation source may be inserted within or associated with the rotary shutter 126. The rotary shutter 126 permits the radiation source 116 to be closely associated with the detector head 104 and is one of the features of the present invention which leads to a reduced measuring gap, g, between the source head 102 and the detector head 104.

As shown in FIGS. 1, 5–7, 11 and 12, the rotary shutter 126 includes a radiation source receiving cavity 152 extending through the rotary shutter 126. The rotary shutter housing 130 includes a radiation source access opening 154 which provides access to the radiation source receiving cavity 152 of the rotary shutter 126 when the rotary shutter is in its closed position. This arrangement advantageously permits insertion and removal of the radiation source 116 and radiation source holder 118 while the rotary shutter 126 is in its closed position. In this way, the source can be more easily shielded from installing personnel for operations involving the radiation source 116. Accordingly, maintenance and repair is facilitated and expedited which is good for service personnel and also results in shorter periods of down time for the associated system 106.

Particular reference will now be made to FIGS. 4–7 for description of radiation source handling and operation of the rotary shutter 126. Assuming that no radiation source 116 has yet been installed in the system 106, the rotary shutter 126 is moved to its closed position shown in FIG. 5. An appropriate shield block is installed or, if already present, is verified as being appropriate for the radiation source to be installed prior to installing the source. The radiation source holder 118 includes a generally square installation projection 156 including an internal female screw thread. A radiation source handling tool 158 includes a radiation source holder end 160 including a male screw thread. The holder end 160 of the tool 158 is threadedly engaged with the installation projection 156 of the radiation source holder 118.

With the bolts 122 removed from the holder/shield combination, the radiation source holder 118 is removed from the health shield 120 using the tool 158, moved to the position shown in FIG. 5 and inserted into the radiation source receiving cavity 152 of the rotary shutter 126 through the radiation source access opening 154 of the rotary shutter housing 130. The tool 158 can include an operation handle 162 spaced from its holder end 160 by an appropriate distance for operator safety and may include a spaced opposite end (not shown) formed to drivingly engage the bolts 122. Once in place as shown in FIG. 6, the radiation source holder 118 is secured in the rotary shutter 126 by means of the bolts 122 or other appropriate fasteners or securing arrangements. Once installed, the radiation source 116 can be moved to emit radiation through the beam source aperture 146 by operating the cylinder 138 to rotate the rotary shutter 126 from its closed position to its opened position shown in FIG. 7.

The detector head 104 of FIG. 2 comprises a housing 164 which has a lower surface defined by a detector sensor plate 166. An ionization chamber 168 is mounted within the housing 164 and supported upon the detector sensor plate 166. The ionization chamber 168 is filled with high purity gas and hermetically sealed in accordance with known techniques. Because of the close proximity of the radiation source 116 and the detector head 104 of the system 106, the ionization chamber 168 can be of smaller size than priorly used chambers with a resulting smaller diameter for its radiation entry window 170. The smaller size of the window 170 results in less bulge from the internal gas pressure which permits the chamber 168 to be positioned more closely to the detector sensor plate 166 further contributing to overall reduction of the measuring gap, g, within the system 106. The smaller size of the chamber 168 also presents less gas volume and inter-electrode capacitance than before which improves the detector operating speed.

A detector window 172 is recessed within the detector sensor plate 166 and closely associated with tuner means comprising a tuner component or window 174 mounted between the detector window 172 and the radiation sensor window 170 in the illustrated embodiment. The tuner means provides for tuning the radiation beam 142 to compensate for geometric characteristics of the radiation source 116 and the detector or ionization chamber 168.

Two different embodiments of the tuner means are illustrated in FIGS. 9 and 10. In FIG. 9, a first embodiment of the tuner means comprises a tuner component 174A made up of a first disk 176 of material which is semi-transparent to radiation emitted by the radiation source 116 and supported at a substantially central point of receipt of the radiation beam by the ionization chamber 168. A second disk 178 of material which is semi-transparent to the radiation emitted by the radiation source 116 is also supported at substantially the central point of receipt of the radiation beam by the ionization chamber 168. The second disk 178 is larger than the first disk 176 and is positioned concentric with the first disk 176. The first and second disks 176, 178 are supported upon material 180 which is substantially transparent to the radiation emitted by the radiation source 116.

In FIG. 10, a second embodiment of the tuner means comprises a tuner component 174B made up of a first strip 182 of material which is semi-transparent to the radiation emitted by the radiation source 116 and a second strip 184 of material which is semi-transparent to the radiation emitted by the radiation source 116 and is supported substantially perpendicular to and centered upon the first strip 182. The second embodiment illustrated in FIG. 10 is particularly applicable to a fan-shaped beam as will be describe hereinafter which defines a narrow band radiation beam. For use with such a fan-shaped radiation beam, the first strip 182 is supported in substantial alignment with the length of the narrow band defined by the beam and is substantially centered upon and extends along at least a substantial portion of the length of the narrow band, and the second strip 184 extends along at least a substantial portion of the width of the narrow band.

A variety of semi-transparent materials can be used to construct the tuner components 174A and 174B with the same or different materials being used for each element of the components. The tuning performed by the tuner components 174A and 174B can be intuitively understood by recognizing that the most energetic portion of the beam will impinge upon the central area of the detector which is the most sensitive. The tuner components 174A and 174B thus intercept and tune the beam such that as the alignment between the source head 102 and the detector head 104 vary relative to one another in the x and y directions, see FIG. 19, the tuned beam energy together with the radiation detection patterns of the detector result in substantially equalized energy reception within conventionally achievable variations in x and y alignment between the source head 102 and the detector head 104.

While the tuning is referred to as tuning the radiation beam since a number of different detectors can be used with the disclosed tuner components 174A, 174B. However, since the tuner components 174A, 174B are incorporated into the detector head 104 and closely associated with the ionization chamber 168, the tuning means or tuner components may also be referred to or thought of as tuning or adjusting the detector sensitivity. The specific dimensions, materials and selection of the tuning means are best performed taking into consideration both the radiation source and the detector to be used for a given measurement application.

In considering the radiation beam for a web measuring system, two beam characteristics are typically traded off against each other. On one hand, the beam should have a large solid angle to generate maximum signal levels having satisfactory signal-to-noise (S/N) ratios. On the other hand, the beam dimension in the cross direction (CD) should be small to provide for detecting streaks which occur in the web 108. Reduction of the CD beam dimension of course reduces the solid angle of the beam and reduces the S/N ratio. In addition, the radiation beam has always been substantially smaller than the radiation detection portion of a detector to be able to tolerate expected amounts of misalignment in the x and y directions. Thus, beams have been generally narrow oftentimes referred to as pencil beams. Beams have also been shaped as cones or conical beams and fan-shaped beams, i.e. beams having a long, narrow radiation pattern, have also been used; but these beams always were formed to be substantially smaller than the detector as noted.

Figure 13:
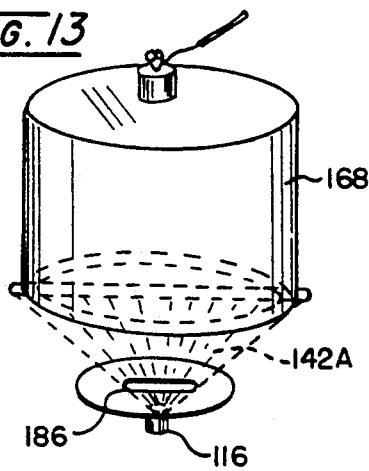
FIGS. 13-18 illustrate generation and detection of a fan-shaped beam of the present invention and how this radiation source/detector arrangement provides composition insensitivity.

In accordance with one aspect of the present invention, a new form of fan-shaped radiation beam may be desirable in given web measurement applications. The fan-shaped radiation beam of the present application is shaped as a narrow beam of radiation such that the width of the beam is substantially less than a radiation receiving portion of a detector and the length of the band is greater than the radiation receiving portion of the detector. Such a fan-shaped radiation beam 142A is shown in perspective view in FIGS. 8 and 13 wherein the radiation source 116 is shaped by aperture means comprising a beam source aperture 186 formed as an elongated slot having rounded ends in the illustrated embodiment. The radiation receiving portion of the ionization chamber 168 is represented by the dashed-dot line representation of its radiation sensor window 170.

Figure 14:
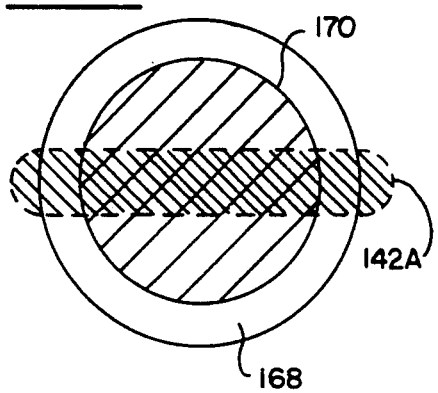

The relationship between the fan-shaped beam 142A and the radiation sensor window 170 of the ionization chamber 168 is also generally shown in FIG. 14. The actual sizing of the fan-shaped radiation beam relative to the detector for optimum performance is preferably determined empirically. Typically the extension of the ends of the fan-shaped beam beyond the detector is small but sufficient to ensure that the ends of the beam extend beyond the detector for all acceptable operating conditions of the system. The width of the fan-shaped beam is selected to provide satisfactory sensitivity for measuring characteristics in the cross direction.

Figure 15:
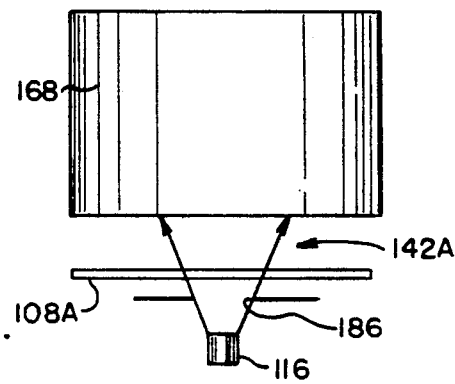
Figure 16:
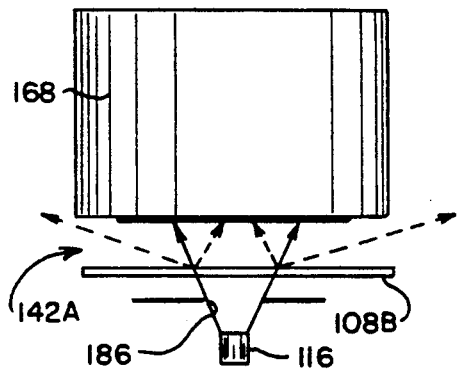
Figure 17:
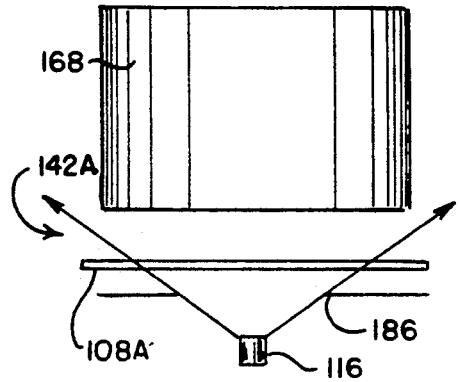
Figure 18:
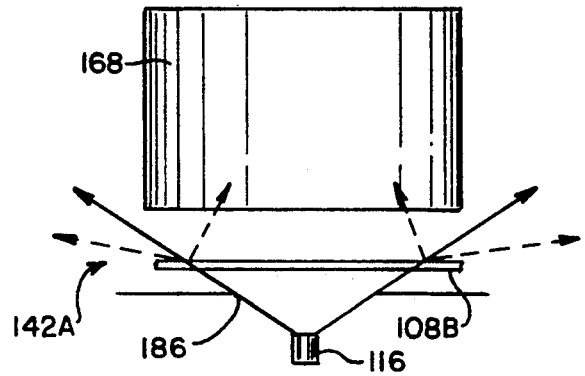

The detector overlapping fan-shaped beam of the present application provides composition insensitivity for web measurement systems as will be explained with reference to FIGS. 15-18. FIGS. 15 and 17 show the fan-shaped beam 142A passing through a web 108A of material which causes low scattering of the beam 142A as it passes through the web 108A. FIGS. 16 and 18 show the fan-shaped beam 142A passing through a web 108B of material which causes high scattering of the beam 108A as it passes through the web 108B. As can be seen by reviewing the low scattering example of FIGS. 15 and 17, almost none of the radiation is lost in the width direction of the beam while some of the radiation is lost in the length direction of the beam at the ends of the fan-shaped beam 142A as shown in FIG. 17.

By comparison, some of the radiation is lost in the width direction of the beam in the high scattering example of FIG. 16. However, some of the radiation which would otherwise have been lost in the length direction of the beam is regained as shown in the high scattering example of FIG. 18. Accordingly, the summation of the radiation detected in the low scattering example of FIGS. 15 and 17 is substantially equal to the radiation detected in the high scattering example of FIGS. 16 and 18. Accordingly, the overlapping fan-shaped beam arrangement is substantially insensitive to the composition or atomic number of the material which makes up the web being measured.

Reliability and operating consistency of a web measuring system incorporating the present invention are better ensured by conditioning the open portion of the air column extending between the radiation source 116 and the ionization chamber 168 through which the web 108 must pass. As shown in FIGS. 1 and 12, the radiation source window 144 is recessed within the radiation source sensor plate 114. As shown in FIGS. 2 and 12, the detector window 172 is recessed within the detector sensor plate 166. First aperture means defines the beam source aperture 146 which is formed in a source aperture plate 188 shown in FIGS. 1, 12 and 20; and second aperture means defines a beam receiving aperture 190 which is formed in a beam receiving aperture plate 192 shown in FIGS. 2, 12 and 21.

A first air manifold 194 passes conditioned air over the radiation source window 144 and out the beam source aperture 146 as indicated by the arrows in FIG. 1. Conditioned air 196 under pressure is received by a positive temperature coefficient (PTC) or other appropriate heater 198 which is controlled to maintain air within the web measuring system at a desired temperature. Temperature controlled air from the first air manifold 194 passes through passageways (not shown) in the rotary shutter housing 130 to the source aperture plate 188. The temperature controlled air enters the source aperture plate 188 via multiple feed points, in the illustrated embodiment four air entry passages 200 shown in FIG. 20. The area 202 between the air entry passages 200 and the beam source aperture 146 serves to pressure balance the temperature controlled air before it is annularly expelled through the aperture 146 as shown by the arrows in FIG. 1.

A second air manifold 204 passes conditioned air over the detector window 172 and out the beam source beam receiving aperture 190 as indicated by the arrows in FIG. 2. Conditioned air 206 under pressure is received by a positive temperature coefficient (PTC) or other appropriate heater 208 which is controlled to maintain air within the web measuring system at a desired temperature. Temperature control can be performed, for example by a microprocessor 209 connected to the heater 208 and a temperature sensor, TS, positioned closely adjacent to air exiting the detector head 104. The microprocessor 209 can also be used to control the heater 198 with the temperature of the air exiting the source head 102 being monitored in a similar manner. Alternately, a separate temperature controller can be provided for the heater 198 of the sensor head 102 if necessary for a given application.

Temperature controlled air from the heater 208 is passed through a passage 210 of a heat exchanger and a first section of tubing 212 to a heat exchanger 214 which is positioned intermediate the ionization chamber 168 and electronic circuit means associated with the ionization chamber 168 for processing signals generated by the chamber 168. The electronic circuit means is enclosed within a housing 216 and is conditioned by the temperature controlled air as the air passes through the heat exchanger 214.

Air from the heat exchanger 214 passes through a second section of tubing 218 to the second air manifold 204 from which temperature controlled air passes through passageways 220 in the beam receiving aperture plate 192. The temperature controlled air enters the beam receiving aperture plate 192 via multiple feed points, in the illustrated embodiment four air entry passages 222 shown in FIG. 21. The area 224 between the air entry passages 222 and the beam receiving aperture 190 serves to pressure balance the temperature controlled air before it is annularly expelled through the aperture 190 as shown by the arrows in FIG. 2.

The air flow described for the source head 102 and the detector head 104 inject conditioned or temperature controlled air in an annular flow pattern in and around the full radiation beam using the same apertures through which the beam passes to stabilize the air density in the air gap of a web measuring system. The air flow over the recessed windows 144 and 172 achieves a flow pattern with positive outflow across the entire areas of the recessed windows 144 and 172 making it substantially impossible for process dirt to enter against the force of the air. The small dimensions of the measurement area confine the air flow to a relatively small volume such that high air speed is obtained, stripping away the boundary air layer carried with the web and shielding the measurement beam from external temperature variability.

The air streams exiting the apertures 144, 172 also form air cushions or bearings on both sides of the web substantially preventing web contact with the source head 102 or detector head 104 further reducing the possibilities of process dirt deposits on the heads.

While the relative positioning of the source head 102 and detector head 104 are tightly maintained by the platform 110, variations in the x, y and z directions do occur. The radiation beam tuning arrangements described above with reference to FIGS. 9 and 10 accommodate variations in the x and y directions. Variations in the z direction or size of the gap, g, also occur and cause a change in the length of the air column and hence the air mass extending between the source head 102 and the detector head 104. To overcome variations in the z direction or gap, g, the air mass is continuously modeled by measuring the size of the gap, g, and utilizing the measured gap size and temperature in conventional equations to calculate the air mass. While the barometric pressure in theory additionally influences these calculations, variations in the barometric pressure are so slow that they can be periodically standardized.

Figure 22:
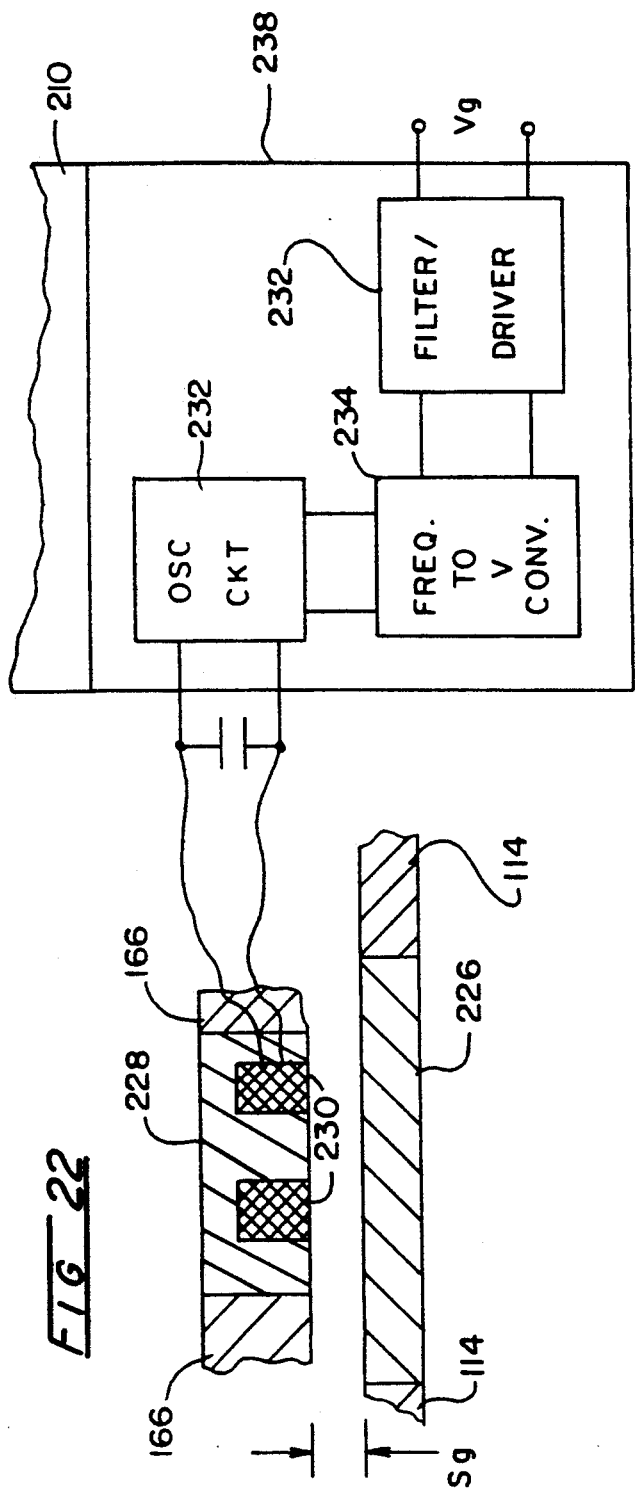
FIG. 22 is a schematic block diagram of a gap sensor for use in a system incorporating the present invention.

The gap measurement is determined by a gap sensor comprising a flat ferrite plate 226 mounted into the radiation source sensor plate 114 and a ferrite cup 228 mounted into the detector sensor plate 166 as shown in FIGS. 1, 2 and 22. A winding 230 in the cup 228 is connected to gap sensing electronics 238 to form the inductive element of an LC oscillator circuit 232, see FIG. 22. The frequency of oscillation of the oscillator circuit 232 is related to the inductance defined by the winding 230 which is a function of the sensor gap, sg, between the cup 228 and the plate 226. As should be apparent, the sensor gap, sg, between the cup 228 and the plate 226 is the same as the gap, g, between the source head 102 and the detector head 104.

Figure 23:
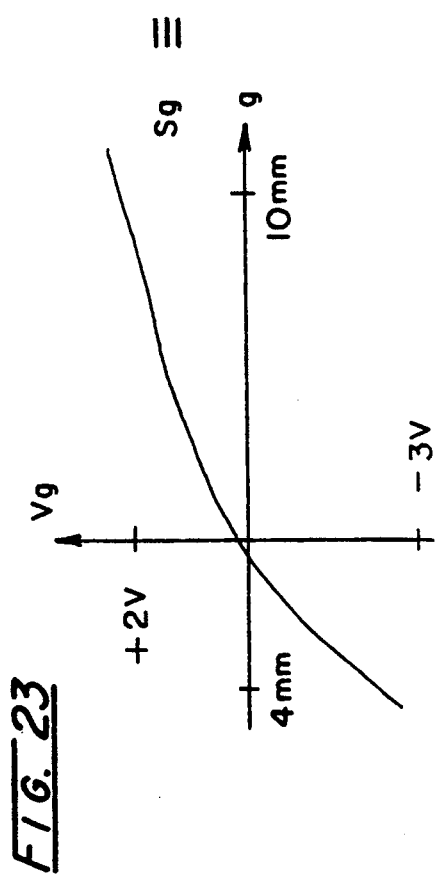
FIG. 23 is a graph of an output signal generated by the gap sensor of FIG. 22.

The output signal from the oscillator circuit 232 is passed to a frequency to voltage converter circuit 234 which generates an output voltage corresponding to the frequency of its input signal. The output voltage from the frequency to voltage converter circuit 234 is passed to a combination low pass filter and output drive circuit 236 which in turn generates an output voltage $V_g$. The output voltage $V_g$ from the circuit 236 is shown in the graph of FIG. 23. A commercially available integrated circuit sold under the designation XR-2211 can be used as the frequency to voltage converter circuit 234 as well as other circuit arrangements as will be apparent to those skilled in the art. However, phase locked loop demodulation provided by the noted integrated circuit ensures good response time which can be a problem in some frequency counter approaches.

An important aspect of the gap measurement system just described is that it must be substantially insensitive to temperature variations. The cup 228 and the plate 226 are exposed to the extremes of the process which is producing the web being monitored and can range in temperature from near room temperature to nearly 300° F. or 148° C. While some prior art gap measurement arrangements may work well at different stable temperatures, they experience substantial errors when temperature gradients exist.

To overcome the temperature and other problems in prior art gap measurement arrangements, the disclosed gap measurement arrangement utilizes relatively large ferrite components with the ferrite plate 226 being substantially larger than the ferrite cup 228 and preferably circular and being substantially concentric with the cup 228 when the source head 102 and the detector head 104 are in alignment. This sizing provides geometric balance to substantially remove sensitivity to alignment in the x and y directions. Temperature stability is enhanced by using selected ferrites to construct the cup 228 and the plate 226. Two examples of ferrite which are preferred for the composition of the cup 228 and the plate 226 are commercially available under the identification H5A ferrite from TDK corporation and 3B7 ferrite from the Philips corporations.

The inductance defined by the winding 230 as described above is capacitively balanced to the oscillator circuit 232 which, for a gap, g, of approximately 7.5 mm, operates at a frequency of approximately 10 kilohertz to ensure good temperature insensitivity. The gap sensing electronics 238 is maintained at a stable temperature by means of the conditioned air which passes through the passage 210 of a heat exchanger which is associated with the gap sensing electronics 238 as shown in FIGS. 2 and 23. Accordingly, the disclosed gap sensing arrangement is sensitive only to variations in the spacing between the source head 102 and the detector head 104 in the z direction, i.e. the gap, g, over a substantial range of temperatures and misalignment in the x and y directions.

Having thus described the methods and apparatus of the present invention in detail and by reference to preferred embodiments thereof, it will be apparent that modifications and variations are possible without departing from the scope of the invention detailed in the appended claims.

What is claimed is:

1. A method of measuring characteristics of a web of sheet material moving in a direction and having first and second sides, said method comprising the steps of:
   positioning a radiation source on said first side of said web of sheet material;
   positioning a detector of said radiation on said second side of said web of sheet material substantially directly opposite to said radiation source;
   shaping radiation emitted from said radiation source to form a beam defining a narrow band of radiation having an expanding length and width as said beam travels from said radiation source;
   spacing said detector from said radiation source such that the width of said band is substantially less than a radiation receiving portion of said detector and the length of said band is greater than said radiation receiving portion of said detector with the result that ends of said band extend beyond opposite sides of said radiation receiving portion of said detector;
   reciprocally scanning said radiation source and said detector in a second direction substantially perpendicular to said first direction;
   detecting radiation received by said detector; and
   determining characteristics of said web of sheet material to be measured from radiation detected by said detector.

2. A method of measuring characteristics of a web of sheet material as claimed in claim 1 further comprising the step of orienting said beam such that the length of said narrow band defined by said beam is substantially aligned with said first direction and the width of said narrow band is substantially aligned with said second direction.

3. A method of measuring characteristics of a web of sheet material as claimed in claim 2 further comprising the step of tuning said beam of radiation to compensate for geometric characteristics of said radiation source and said detector.

4. A method of measuring characteristics of a web of sheet material as claimed in claim 3 wherein the step of tuning said beam of radiation comprises the steps of:
   positioning a first disk of material which is semi-transparent to said radiation at a substantially central point of receipt of said beam by said detector; and
   positioning a second disk of material which is semi-transparent to said radiation at a substantially central point of receipt of said beam by said detector, said second disk being larger than said first disk and positioned concentric with said first disk.

5. A method of measuring characteristics of a web of sheet material as claimed in claim 3 wherein the step of tuning said beam of radiation comprises the steps of:
   positioning a first strip of material which is semi-transparent to said radiation in substantial alignment with the length of said narrow band defined by said beam, said first strip being substantially centered upon and extending along at least a substantial portion of the length of said narrow band; and positioning a second strip of material which is semi-transparent to said radiation substantially perpendicular to said first strip in substantial alignment with the center of said narrow band defined by said beam, said second strip extending along at least a substantial portion of the width of said narrow band.

6. A method of measuring characteristics of a web of sheet material as claimed in claim 1 further comprising the step of supporting said radiation source in a rotating shutter.

7. A method of measuring characteristics of a web of sheet material as claimed in claim 6 further comprising the steps of forming said rotating shutter to permit access to said radiation source when said shutter is rotated to a closed position to thereby facilitate placement of said radiation source into said rotating shutter and removal of said radiation source from said rotating shutter.

8. A method of measuring characteristics of a web of sheet material as claimed in claim 1 further comprising the steps of:

providing a radiation source sensor plate for performing the step of positioning said radiation source, said radiation source sensor plate defining a beam source aperture through which said beam is emitted;

providing a recessed radiation source window within said radiation source sensor plate; and defining a first air manifold associated with said radiation source sensor plate for routing conditioned air over said recessed radiation source window and outwardly through said beam source aperture.

9. A method of measuring characteristics of a web of sheet material as claimed in claim 8 further comprising the steps of:

providing a detector sensor plate for performing the step of positioning said detector, said detector sensor plate defining a beam receiving aperture through which said beam is received;

providing a recessed detector window within said detector sensor plate; and defining a second air manifold associated with said detector sensor plate for routing conditioned air over said recessed detector window and outwardly through said beam receiving aperture.

10. A method of measuring characteristics of a web of sheet material as claimed in claim 9 further comprising the steps of:

providing electronic circuit means associated with said detector for processing signals representative of radiation detected by said detector to determine characteristics of said web;

routing conditioned air to said electronic circuit means to regulate the temperature of said electronic circuit means and thereby enhance the reliability of said electronic circuit means and stabilizes web characteristic measurements; and routing said conditioned air to said second air manifold from said electronic circuit means.

11. A method of measuring characteristics of a web of sheet material moving in a first direction and having first and second sides, said method comprising the steps of:

supporting a rotating shutter on said first side of said web of sheet material, said shutter being rotatably movable between an opened measuring position and a closed position and having a radiation source receiving cavity extending therethrough from a radiation source access end to a radiation emitting end, said radiation emitting end being directed toward said web of sheet material when said shutter is in said opened measuring position and being directed toward a radiation shield when in said closed position;

supporting a detector of said regulation on said second side of said web of sheet material substantially directly opposite to said shutter;

rotating said shutter to said closed position;

inserting a radiation source into said radiation source receiving cavity in said rotating shutter while said shutter is in said closed position, said radiation source entering through said radiation source access of said cavity and being positioned adjacent to said radiation emitting end of said cavity;

rotating said shutter to said opened position to closely associate the radiation emitting end of said cavity and thereby said radiation source with said detector;

reciprocally scanning said rotating shutter and said detector in a second direction substantially perpendicular to said first direction;

detecting radiation received by said detector from said closely associated radiation source;

determining characteristics of said web of sheet material to be measured from radiation detected by said detector;

shaping radiation emitted from said radiation source to form a beam defining a narrow band of radiation having an expanding length and width as said beam travels from said radiation source; and spacing said detector from said radiation source such that the width of said band is substantially less than a radiation receiving portion of said detector and the length of said band is greater than said radiation receiving portion of said detector with the result that ends of said band extend beyond opposite sides of said radiation receiving portion of said detector.

12. A method of measuring characteristics of a web of sheet material moving in a first direction and having first and second sides, said method comprising the steps of:

positioning a radiation source on said first side of said web of sheet material;

positioning a detector of said radiation on said second side of said web of sheet material substantially directly opposite to said radiation source;

tuning a radiation beam emitted by said radiation source to compensate for geometric characteristics of said radiation source and said detector in two dimensions by positioning tuning component means between said source and said detector, said tuning component means comprising first and second semi-transparent radiation transmitting means with said first semi-transparent radiation transmitting means overlaying said second semi-transparent radiation transmitting means over a central portion thereof;

reciprocally scanning said radiation source and said detector in a second direction substantially perpendicular to said first direction;

detecting radiation received by said detector; and determining characteristics of said web of sheet material to be measured from radiation detected by said detector.

13. A method of measuring characteristics of a web of sheet material as claimed in claim 12 wherein the step of tuning said radiation beam comprises the steps of:
positioning a first disk of material which is semi-transparent to said radiation at a substantially central point of receipt of said beam by said detector; and
positioning a second disk of material which is semi-transparent to said radiation at a substantially central point of receipt of said beam by said detector, said second disk being larger than said first disk and positioned concentric with said first disk.

14. A method of measuring characteristics of a web of sheet material as claimed in claim 12 wherein the step of tuning said radiation beam comprises the steps of:
positioning a first strip of material which is semi-transparent to said radiation in substantial alignment with the length of said narrow band defined by said beam, said first strip being substantially centered upon and extending along at least a substantial portion of the length of said narrow band; and
positioning a second strip of material which is semi-transparent to said radiation substantially perpendicular to said first strip in substantial alignment with the center of said narrow band defined by said beam, said second strip extending along at least a substantial portion of the width of said narrow band.

15. A method of measuring characteristics of a web of sheet material as claimed in claim 12 further comprising the steps of:
shaping radiation emitted from said radiation source to form a beam defining a narrow band of radiation having an expanding length and width as said beam travels from said radiation source; and
spacing said detector from said radiation source such that the width of said band is substantially less than a radiation receiving portion of said detector and the length of said band is greater than said radiation receiving portion of said detector with the result that ends of said band extend beyond opposite sides of said radiation receiving portion of said detector.

16. A system for measuring characteristics of a web of sheet material moving in a first direction and having first and second sides, said system comprising:
radiation source means positioned on said first side of said web of sheet material for emitting a beam of radiation;
detector means for detecting said radiation, said detector means being positioned on said second side of said web of sheet material substantially directly opposite to said radiation source means;
first aperture means associated with said radiation source means for shaping said beam of radiation to form a beam defining a narrow band of radiation having an expanding length and width as said beam travels from said radiation source means, said radiation source means, said detector means and said first aperture means being sized and spaced relative to one another such that the width of said narrow band of radiation is substantially less than said detector means and the length of said narrow band of radiation is greater than said detector means with ends of said narrow band of radiation extending beyond opposite sides of said detector means; and
scanner means for reciprocally scanning said radiation source means and said detector means across said web of material in a second direction substantially perpendicular to said first direction.

17. A system for measuring characteristics of a web of sheet material as claimed in claim 16 wherein said first aperture means is aligned to emit said beam such that the length of said beam is substantially aligned with said first direction.

18. A system for measuring characteristics of a web of sheet material as claimed in claim 17 further comprising tuner means for tuning said beam of radiation to compensate for geometric characteristics of said radiation source means and said detector means.

19. A system for measuring characteristics of a web of sheet material as claimed in claim 18 wherein said tuner means comprises a tuning component supported between said radiation source means and said detector means and comprising:
a first disk of material which is semi-transparent to said radiation and supported at a substantially central point of receipt of said beam by said detector means; and
a second disk of material which is semi-transparent to said radiation and supported at a substantially central point of receipt of said beam by said detector means, said second disk being larger than said first disk and positioned concentric with said first disk.

20. A system for measuring characteristics of a web of sheet material as claimed in claim 18 wherein said tuner means comprises a tuning component supported between said radiation source means and said detector means, said tuning component comprising:
a first strip of material which is semi-transparent to said radiation and supported in substantial alignment with the length of said narrow band defined by said beam, said first strip being substantially centered upon and extending along at least a substantial portion of the length of said narrow band; and
a second strip of material which is semi-transparent to said radiation and supported substantially perpendicular to said first strip in substantial alignment with the center of said narrow band defined by said beam, said second strip extending along at least a substantial portion of the width of said narrow band.

21. A system for measuring characteristics of a web of sheet material as claimed in claim 16 further comprising rotating shutter means for supporting said radiation source means.

22. A system for measuring characteristics of a web of sheet material as claimed in claim 21 wherein said rotating shutter means comprises a cylindrical member mounted for rotation about a central axis, said cylindrical member being rotatable about said central axis between a shutter opened position and a shutter closed position and including a radiation source means receiving cavity extending therethrough which cavity is accessible when said cylindrical member is rotated to said shutter closed position whereby said radiation source means can be inserted into and removed from said rotating shutter while said shutter is in its closed position.

23. A system for measuring characteristics of a web of sheet material as claimed in claim 16 further comprising:
a radiation source sensor plate associated with said radiation source means, said radiation source sensor plate supporting said first aperture means which defines a beam source aperture through which said beam is emitted;

a radiation source window recessed within said radiation source sensor plate adjacent to said beam source aperture; and first air manifold means defined by said first aperture means and said radiation source sensor plate for routing conditioned air over said recessed radiation source window and outwardly through said beam source aperture.

24. A system for measuring characteristics of a web of sheet material as claimed in claim 23 further comprising:

a detector sensor plate associated with said detector means, said detector sensor plate supporting second aperture means for defining a beam receiving aperture through which said beam is received;

a detector window recessed within said detector sensor plate; and second air manifold means associated with said second aperture means, said second air manifold means and said second aperture means cooperatively providing for routing conditioned air over said recessed detector window and outwardly through said beam receiving aperture.

25. A system for measuring characteristics of a web of sheet material as claimed in claim 24 further comprising:

circuit means associated with said detector means for processing signals representative of radiation detected by said detector means to determine characteristics of said web; and conduit means for routing conditioned air initially to said electronic circuit means to regulate the temperature of said electronic circuit means and thereby enhance reliability of said electronic circuit means and stabilize web characteristic measurements performed by said system and then to said second air manifold means.

26. A system for measuring characteristics of a web of sheet material as claimed in claim 25 wherein said conduit means includes heat exchanger means associated with said electronic circuit means for regulating the temperature of said electronic circuit means with no direct contact between said conditioned air and said electronic circuit means.

27. A system for measuring characteristics of a web of sheet material moving in a first direction and having first and second sides, said system comprising:

radiation source means for emitting a beam of radiation;

rotating shutter means for supporting said radiation source means on said first side of said web of sheet material for emitting said beam of radiation through said web, said rotating shutter means comprising a housing member mounted for rotation about an axis, said housing member being rotatable about said axis between a shutter opened position and a shutter closed position and including a radiation source means receiving cavity extending through said housing member from a radiation source access end to a radiation emitting end, said cavity being accessible for insertion and removal of said radiation source means through said radiation source access end when said housing member is rotated to said shutter closed position;

detector means for detecting said radiation, said detector means being positioned on said second side of said web of sheet material substantially directly opposite to and closely associated with said radiation source means when said rotating shutter means is in said opened position;

scanner means for reciprocally scanning said rotating shutter means and said detector means across said web of material in a second direction substantially perpendicular to said first direction; and aperture means associated with said radiation source means for shaping said beam of radiation to form a beam defining a narrow band of radiation having an expanding length and width as said beam travels from said radiation source means, said radiation source means, said detector means and said aperture means being sized and spaced relative to one another such that the width of said narrow band of radiation is substantially less than said detector means and the length of said narrow band of radiation is greater than said detector means with ends of said narrow band of radiation extending beyond opposite sides of said detector means.

28. A system for measuring characteristics of a web of sheet material moving in a first direction and having first and second sides, said system comprising:

radiation source means positioned on said first side of said web of sheet material for emitting a beam of radiation;

detector means for detecting said radiation, said detector means being positioned on said second side of said web of sheet material substantially directly opposite to said radiation source means;

tuner means for tuning said beam of radiation to compensate for geometric characteristics of said radiation source means and said detector means in two dimensions, said tuner means comprising first and second semi-transparent radiation transmitting means with said first semi-transparent radiation transmitting means overlaying said second semi-transparent radiation transmitting means over a central portion thereof; and scanner means for reciprocally scanning said radiation source means and said detector means across said web of material in a second direction substantially perpendicular to said first direction.

29. A system for measuring characteristics of a web of sheet material as claimed in claim 28 wherein said tuner means comprises a tuning component supported between said radiation source means and said detector means and comprising:

a first disk of material which is semi-transparent to said radiation and supported at a substantially central point of receipt of said beam by said detector means; and a second disk of material which is semi-transparent to said radiation and supported at a substantially central point of receipt of said beam by said detector means, said second disk being larger than said first disk and positioned concentric with said first disk.

30. A system for measuring characteristics of a web of sheet material as claimed in claim 28 wherein said tuner means comprises a tuning component supported between said radiation source means and said detector means, said tuning component comprising:

a first strip of material which is semi-transparent to said radiation and supported in substantial alignment with the length of said narrow band defined by said beam, said first strip being substantially centered upon and extending along at least a substantial portion of the length of said narrow band; and a second strip of material which is semi-transparent to said radiation and supported substantially perpendicular to said first strip in substantial alignment with the center of said narrow band defined by said beam, said second strip extending along at least a substantial portion of the width of said narrow band.

31. A system for measuring characteristics of a web of sheet material as claimed in claim 28 further comprising aperture means associated with said radiation source means for shaping said beam of radiation to form a beam defining a narrow band of radiation having an expanding length and width as said beam travels from said radiation source means, said radiation source means, said detector means and said aperture means being sized and spaced relative to one another such that the width of said narrow band of radiation is substantially less than said detector means and the length of said narrow band of radiation is greater than said detector means with ends of said narrow band of radiation extending beyond opposite side of said detector means.

32. A system for measuring characteristics of a web of sheet material moving in a first direction and having opposite sides, said system comprising:

radiation source means positioned on one side of said web of sheet material for emitting a beam of radiation;

detector means for detecting said radiation, said detector means being positioned on a side opposite to said one side of said web of sheet material substantially directly opposite to said radiation source means and spaced therefrom by a gap;

gap sensing means for measuring said gap between said radiation source and detector means, said gap sensing means comprising:
- a ferrite cup positioned on one side said web of sheet material;
- a winding positioned within said ferrite cup;
- a ferrite plate positioned opposite to said ferrite cup, said ferrite plate being circular and larger in diameter than said ferrite cup;
- an LC oscillator circuit connected to said winding for generating a signal having a frequency representative of said gap;
- frequency monitoring means connected to said LC oscillator circuit for generating a signal representative of said gap; and scanner means for reciprocally scanning said radiation source means and said detector means across said web of material in a second direction substantially perpendicular to said first direction.

33. A system for measuring characteristics of a web of sheet material as claimed in claim 32 wherein said ferrite cup and said ferrite plate are constructed from temperature stable ferrite material.

* * * * *

UNITED STATES PATENT AND TRADEMARK OFFICE
CERTIFICATE OF CORRECTION

PATENT NO.   : 5,233,195
DATED        : August 3, 1993
INVENTOR(S)  : Ake A. Hellstrom, Wim Muller, Steven P. Sturm, Alan M. Reid It is certified that error appears in the above-indentified patent and that said Letters Patent is hereby corrected as shown below:

Col. 16, Line 14, "in a direction" should be --in a first direction--.
Col. 18, Line 12, "said regulation" should be --said radiation--.
Col. 21, Line 27, "circuit means" should be --electronic circuit means--.
Col. 23, Line 21, "opposite side" should be --opposite sides--.

Signed and Sealed this

Twenty-ninth Day of March, 1994

Attest:

BRUCE LEHMAN

Attesting Officer    Commissioner of Patents and Trademarks